US008579804B2

(12) United States Patent
Desmond, III

(10) Patent No.: US 8,579,804 B2
(45) Date of Patent: Nov. 12, 2013

(54) VARIABLE LENGTH NEPHROSTOMY SHEATH

(75) Inventor: Joseph P. Desmond, III, Bloomington, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 2522 days.

(21) Appl. No.: 10/601,410

(22) Filed: Jun. 23, 2003

(65) Prior Publication Data

US 2004/0260246 A1 Dec. 23, 2004

(51) Int. Cl.
*A61B 1/00* (2006.01)

(52) U.S. Cl.
USPC .......................................................... 600/184

(58) Field of Classification Search
USPC .................... 600/184; 606/185, 108; 604/174; 623/1.11, 1.12, 1.23
See application file for complete search history.

(56) References Cited

U.S. PATENT DOCUMENTS

| 3,800,799 | A |   | 4/1974  | McWhorter |           |
|-----------|---|---|---------|-----------|-----------|
| 3,982,544 | A |   | 9/1976  | Dyck      | 128/349   |
| 4,498,902 | A | * | 2/1985  | Ash et al.| 604/164.05|
| 4,600,402 | A |   | 7/1986  | Rosenberg | 604/96    |
| 4,652,258 | A |   | 3/1987  | Drach     | 604/53    |
| 4,710,171 | A |   | 12/1987 | Rosenberg | 604/117   |
| 4,738,667 | A |   | 4/1988  | Galloway  | 604/281   |
| 5,197,963 | A |   | 3/1993  | Parins    | 606/46    |
| 5,250,025 | A |   | 10/1993 | Sosnowski et al. | 604/51 |
| 5,385,562 | A |   | 1/1995  | Adams et al. | 604/280 |
| 5,395,342 | A |   | 3/1995  | Yoon      |           |
| 5,562,640 | A | * | 10/1996 | McCabe et al. | 604/541 |
| 5,695,475 | A | * | 12/1997 | Best et al. | 604/198 |
| 5,728,129 | A |   | 3/1998  | Summers   | 606/170   |
| 5,765,682 | A |   | 6/1998  | Bley et al. | 206/363 |
| 5,827,227 | A |   | 10/1998 | DeLago    | 604/104   |
| 5,957,888 | A | * | 9/1999  | Hinchliffe | 604/117 |
| 5,964,740 | A | * | 10/1999 | Ouchi     | 604/264   |
| 5,993,471 | A | * | 11/1999 | Riza et al. | 606/185 |
| 6,090,072 | A |   | 7/2000  | Kratoska et al. | 604/164 |
| 6,436,119 | B1|   | 8/2002  | Erb et al. |          |
| 6,869,395 | B2| * | 3/2005  | Page et al. | 600/127 |
| 6,875,219 | B2| * | 4/2005  | Arramon et al. | 606/92 |
| 6,896,665 | B2| * | 5/2005  | Picha et al. | 604/104 |
| 2001/0029353 | A1 | * | 10/2001 | Peterson | 604/164.11 |

FOREIGN PATENT DOCUMENTS

WO WO 9836785     8/1998
WO WO 9836785 A1 * 8/1998

OTHER PUBLICATIONS

International Search Report for PCT Application No. US2004/020038, filed Jun. 23, 2004, 4 pages.

* cited by examiner

*Primary Examiner* — Ryan Severson
*Assistant Examiner* — Julie A Szpira

(57) ABSTRACT

An adjustable sheath assembly sized to accept a medical instrument and adapted for insertion into a body of a patient for maintaining a passageway therein. The device includes a first hollow member having a first length, and a second hollow member having a second length, the first and second members being coaxially joined together through a length adjustment element. At least one of the first and second hollow members is sized to accept a medical instrument. The length adjustment element allows for the length of the sheath assembly to be fitted to bodies of various sizes by adjusting the length prior to insertion into the patients body. A properly adjusted length ensures that at least a portion of the sheath assembly remains outside of the patient's body.

36 Claims, 8 Drawing Sheets

VARIABLE LENGTH NEPHROSTOMY SHEATH

TECHNICAL FIELD

The present invention relates generally to medical devices for maintaining a passageway to gain access to portions of a patient's body by a physician, for example maintaining percutaneous access to the kidney for performing a nephrostomy. In particular, the present invention relates to adjustable sheath assemblies adapted for maintaining a passageway open, to enable medical instruments to be used for treating the patient.

BACKGROUND INFORMATION

An increasing number of surgical procedures are being performed using minimally invasive techniques. Many of these techniques involve a physician operating internally on a patient's body through a relatively small opening. The small opening can be obtained percutaneously by opening a tract into a patient's body, by utilizing an existing body lumen, or by a combination of both techniques. Once a tract has been opened, a sheath is often necessary to maintain the tract open, for example to facilitate insertion, placement, and removal of catheters and other medical instruments, such as an arthroscope or a stent. A sheath is also useful for draining fluids from a body, such as urine from a kidney or bladder, and for inserting fluids, such as a contrasting agent for a radiograph, into a body.

One particular medical procedure using a sheath is a nephrostomy, in which an opening is surgically formed between a renal pelvis and the outside of the body. Generally, a small tract is made with a needle, or trocar, through a patient's body (i.e., the back), through the cortex of the kidney, and into the renal pelvis. Once formed, the small tract is expanded to a predetermined size to accommodate medical instruments and/or removal of a renal calculi (i.e., a stone). Once the tract has been expanded, a sheath can be inserted along the length of the tract extending from outside the patient's body to the internal target area. The expanding instruments can then be removed, for example, through the sheath. A guide wire, however, is often left within the sheath to facilitate repositioning of the sheath should that be necessary, and to facilitate insertion and removal of medical instruments. Once properly installed, a physician is then free to perform the intended medical procedure through the tract formed by the sheath. Upon completion of the procedure, the sheath is removed from the patient's body and any incision is closed.

Sheaths as described above are commercially available in standard or preselected sizes, the diameters and lengths typically depending on a particular application. Exemplary sheaths include the FLEXOR® ureteral access sheath available in internal diameters ranging from 9.5 French units (Fr) to 12.0 Fr, and lengths ranging from 20 cm (order no. FUS-095020) to 55 cm (order no. FUS-120055), the sheath of the N-CIRCLE® Nitinol Tipless Stone Extractor (e.g., order no. NTSE-022115-UDH), and the N-Force® Nitinol Helical Stone Extractor (e.g., order no. NFHSES-032115-3W-UDH), all manufactured by Cook Urological, Inc., of Spencer, Ind. Other sheaths are commercially available, such as the Examining Ureteral Sheath (catalog no. HUS-10S) and the Operating Ureteral Sheath (catalog no. HUS-12S), both manufactured by ACMI Corp. of Southborough, Mass.

Unfortunately, these and other commercially available sheaths are unavailable for some patients, as the standard sizes are inadequate. In particular, the commercially available nephrostomy sheaths can be too short for obese patients. Use of a sheath that is too short can result in procedural complications. For example, a sheath extending outside of the patient's body can pull away from a target location within a patient's body. Alternatively, a sheath remaining fixed to a target location can recess completely within a patient's body. Either scenario would unnecessarily complicate the related procedure and increase risk to the patient.

SUMMARY OF THE INVENTION

An adjustable sheath assembly for access to the inside of a patient's body has been developed, which is useful in a variety of medical applications including, but not limited to, the exchange of medical instruments, diagnostic devices, and the drainage of fluids and removal of objects (e.g., kidney stones). The sheath assembly can be used to provide percutaneous access to the inside of the body, or it can be used in natural body orifices, or it can be used in a combination of both. The variable length allows the sheath assembly to be fitted to patients of various sizes, including small children, and/or obese patients. The properly fitted sheath assembly extends from outside the body to a treatment site inside the body, Thus, the properly fitted sheath assembly allows a physician to access the external end of the sheath assembly, for inserting and/or removing medical instruments through the sheath to remotely perform diagnosis and/or medical procedures at the treatment. Applications include urological procedures, stent delivery, and laproscopic procedures.

In general, in one aspect, the invention relates to a medical device adapted for insertion into a body of a patient for maintaining a passageway therein. The device includes a first hollow member having a first length, a proximal end, and a distal end. When inserted into a patient's body, at least a portion of the proximal end remains outside of the body. The device also includes a second hollow member having a second length, a proximal end, and a distal end; and a length adjustment element. In one embodiment, at least one of the first and second hollow members is sized to accept a medical instrument. The length adjustment element is attached to both the distal end of the first hollow member and the proximal end of the second hollow member. The length adjustment element coaxially joins together the first and second hollow members in an adjustable manner, such that the joined members have a combined length that is selectable and longer than the longest of the first length and the second length.

In one embodiment, at least one of the first hollow member and the second hollow member comprises a cylinder. At least one of the first and second hollow members can be made of a semi-rigid material. Preferably, the semi-rigid material includes non-stick properties (i.e., the material is substantially inert), thereby facilitating insertion, placement, and removal within a patient's body, and allowing for the unhindered passage of medical instruments. Some examples of suitable semi-rigid materials include polytetrafluoroethylene (PTFE), fluorinated ethylene propylene (FEP), polyethylene, plastics, and combinations thereof.

In another embodiment, the distal end of the first hollow member includes a beveled edge adapted to facilitate insertion into the body. The distal end of the second hollow member defines an end face, which resides in a plane. In one embodiment, the plane and the longitudinal axis define an acute angle therebetween to facilitate insertion into the body. In some embodiments, the end face includes a chamfered edge to facilitate manipulation within the body.

In one embodiment, the length adjustment element includes a first thread formed along at least a portion of the distal end of the first member. The length adjustment element also includes a second thread for mating with the first thread, the second thread being formed along at least a portion of the proximal end of the second member. In another embodiment, the length adjustment element comprises a notch-and-detent system. The notch-and-detent system includes at least one detent extending radially about at least a portion of one end of one of the first and second members. The notch-and-detent system also includes several notches extending radially over at least a portion of one end of the other of the first and second members. The notches can be formed to allow travel of the detent in either of two opposing direction across the notch, for example, allowing for expansion and contraction of the combined first and second members. Alternatively, the notches can be formed to allow for travel of the detent in only one of two opposite directions across the notch, for example, allowing for a contraction, but not expansion, of the length of the combined first and second members.

In another embodiment, the length adjustment element includes an interference fit formed by an interior surface of the distal end of the first member overlapping a portion of an exterior surface of the proximal end of the second member. The overlapping surfaces provide a frictional fit. The frictional fit can include a slot defined by at least one of the distal end of the first member and the proximal end of the second member. The slot can extend axially along the at least one of the first and second members from one end of the member. Such a slot enables a radial deformation of the respective end.

In yet another embodiment, an elastomeric element is disposed between the distal end of the first member and the proximal end of the second member. The elastomeric element is in frictional communication with both the distal end of the first member and the proximal end of the second member, allowing for adjustment of the combined length.

In some embodiments, the medical device further includes a locking element. The locking element allows for a selectable length to be fixed once selected. The locking device can include a wedge, insertable and providing an interference fit between at least one of the distal end of the first member and the adjustable element, and the proximal end of the second member and the adjustable element. Alternatively or additionally, the locking device can include a post-and-groove system. In such a post-and-groove system, the post is slidable along at least a portion of the groove between a free position and a locked position.

In still another embodiment, the combination of the first member, the length adjustment element, and the second member are substantially fluid tight.

In another aspect, the invention relates to a medical device adapted for insertion into a body of a patient for maintaining a passageway therein. The device includes a first hollow member for providing an unobstructed passageway from outside of the patient's body to the inside when inserted. The device also includes a second hollow member in adjustable communication with the first hollow member for extending the unobstructed passageway provided by the first hollow member to a predetermined internal location. In one embodiment, at least one of the first and second hollow members is sized to accept a medical instrument.

In another embodiment, the first hollow member has a proximal end and a distal end, with the distal end including a thread over at least a portion thereof. The second hollow member also has a proximal end and a distal end, with the proximal end including a mating thread over at least a portion thereof. The first and second hollow members are adjustably joined through the mating threads.

In another embodiment, the first hollow member has a proximal end and a distal end, and the second hollow member also has a proximal end and a distal end. At least one of the distal end of the first member and the proximal end of the second member includes several notches over at least a portion thereof. The other of the distal end of the first member and the proximal end of the second member includes a detent. The first and second members are adjustably joined through the detent and plurality of notches.

In yet another embodiment, one end of the first hollow member is in slidable engagement with one end of the second hollow member. An overall length of the combined first and second members is thus adjustable through the slidable engagement of the two members.

BRIEF DESCRIPTION OF THE DRAWINGS

The invention is pointed out with particularity in the appended claims. The advantages of the invention may be better understood by referring to the following description taken in conjunction with the accompanying drawing in which:

DETAILED DESCRIPTION

A variable length sheath assembly can be fitted to patients of various sizes, including small children, and/or obese patients. A properly fitted sheath assembly extends along an opening from outside the body to a treatment site inside the body, allowing a physician to access the external end of the sheath assembly. The sheath enables the physician to perform a diagnosis and/or medical procedure at a treatment site within a patient's body in a minimally invasive manner. At least a portion of the sheath is sized to accept medical instruments. By inserting and/or removing medical instruments into and/or through the sheath, the physician can operate remotely through the passageway provided by the sheath. The sheath provides stability and a smooth passageway along the opening, thereby facilitating repeated insertion, positioning, and removal of medical instruments.

Figure 1:
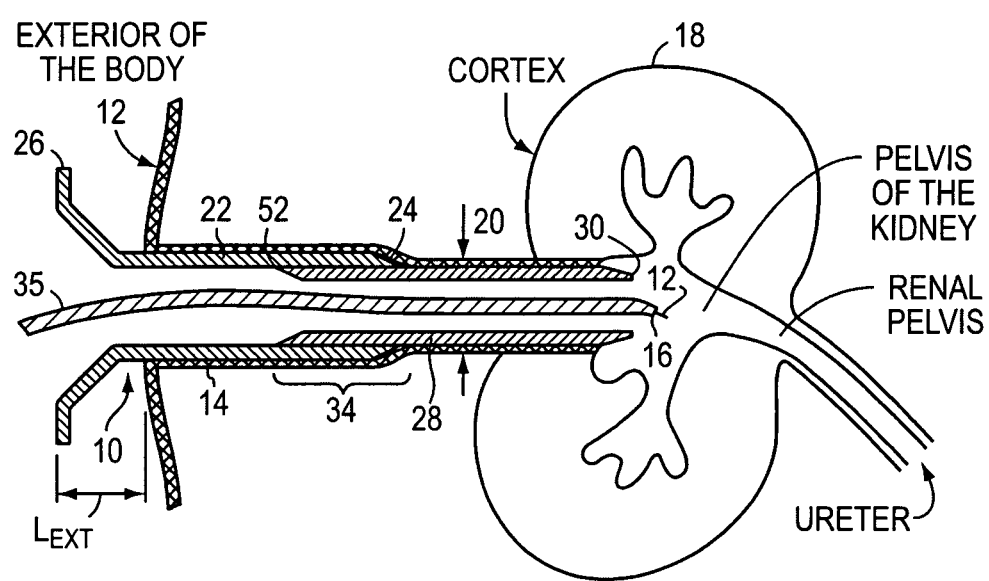
FIG. 1 illustrates a cross-sectional view of one embodiment of an adjustable sheath assembly having a length-adjustment member, the sheath assembly having a distal end installed within a body and a proximal end extending outside the body.

Referring to FIG. 1, a variable length sheath assembly 10 providing percutaneous access to a patient's body 12 is advanced through a body tract 14 to a predetermined target location, such as a renal pelvis 16 of a kidney 18. When installed in its predetermined location, a portion of the variable length sheath assembly 10 remains exposed outside of the patient's body by some length $L_{EXT}$. A percutaneous body tract 14 can first be established by an interventional instrument, such as a needle or trocar (not shown). Alternatively, the variable length sheath assembly 10 can be used through a natural body lumen (e.g., urethra) for procedures in which percutaneous access is not required. In either instance, the tract is generally first expanded to a predetermined diameter 20 before the variable length sheath assembly 10 is inserted. The tract can be expanded using an of the available dilation systems including balloons and expanding sleeves.

The variable length sheath assembly 10 includes a first elongated hollow member 22 having distal and proximal ends 24 and 26 respectively. The variable length sheath assembly 10 also includes a second elongated hollow member 28 having distal and proximal ends 30 and 32 respectively. The first and second elongated hollow members 22 and 28 are coaxially aligned and adjustably joined together through a length adjustment element 34. The combined first and second elongated hollow members 22 and 28, together with the length adjustment element 34 form the variable length sheath assembly 10—itself an overall, single elongated hollow device.

The first and second elongated hollow members 22 and 28 are typically formed as cylinders having a predetermined cross-sectional shape. In one embodiment, the cross-sectional shape is substantially circular. In other embodiments, the cross-sectional shape can be elliptical. In yet other embodiments, the cross-sectional shape can be triangular, rectangular, polygonal, or even an irregular shape. It is also conceivable that the cross-sectional shape and/or dimensions can vary along the axis of the variable length sheath assembly 10. For example, the proximal end 26 of the variable length sheath assembly 10 can have a relatively large size and/or irregular shape to accommodate a medical instrument, whereas the distal end 30 can have a relatively smaller size and/or regular shape to minimize invasion into a target location.

Figure 2:
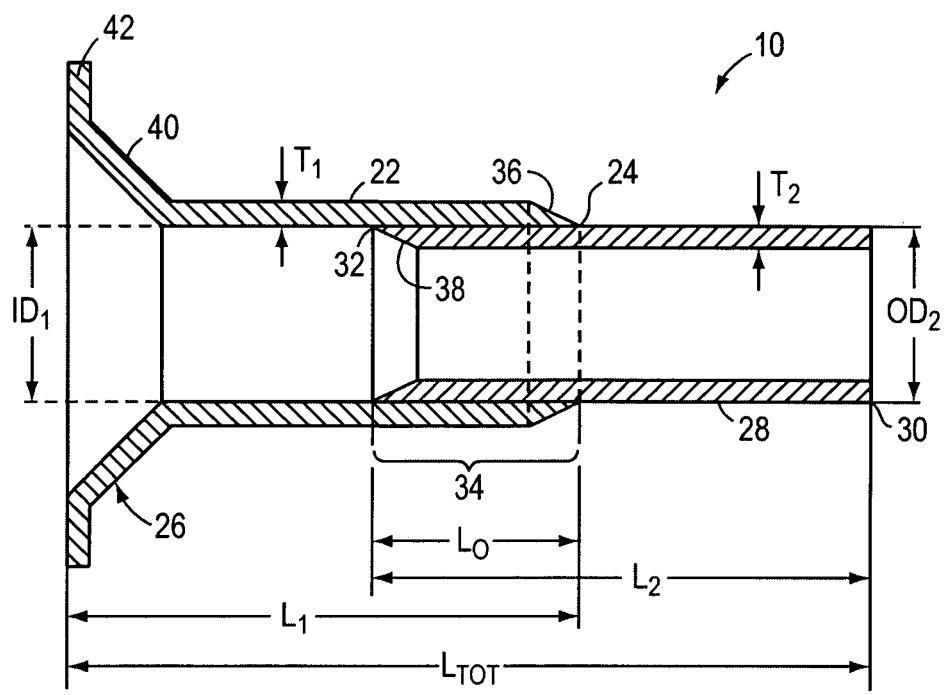
FIG. 2 illustrates a more detailed cross-sectional view of one embodiment of the adjustable sheath assembly illustrated in FIG. 1.

Referring now to FIG. 2, the first elongated hollow member 22 has a first inside diameter ($ID_1$) and a first length $L_1$. The second elongated hollow member 28 has a second outside diameter ($OD_2$) and a second length $L_2$. In one embodiment, $ID_1$ is wider than $OD_2$, such that the proximal end 32 of the second elongated hollow member 28 fits within the distal end 24 of the first elongated hollow member 22. In other embodiments, in which the elongated hollow members 22 and 28 are formed from a semi-flexible material, the diameters $ID_1$ and $OD_2$, can be substantially the same dimension, such that $ID_1$ can contract slightly upon deformation of the semi-flexible material, and/or $OD_2$ can likewise expand slightly thereby allowing the coaxial union of the respective ends of the elongated hollow members 22 and 28.

At least a portion of the sheath assembly 10 is sized to accept a medical instrument. In one embodiment, the inside diameter of the first elongated hollow member 22 can be large enough to accept a medical instrument. For example, a fluid injector for injecting a fluid through the sheath assembly 10 into the target region can be inserted into the proximal end of the first elongated hollow member 22 without extending through the second elongated hollow member 28. The fluid injector, once positioned, can inject a fluid, such as a dye, through the sheath assembly 10 and into the target region located at the distal end of the sheath assembly 10.

In some embodiments, the inside diameter of the first elongated hollow member 22 and/or the inside diameter of the second elongated hollow member 28 can vary along a central axis. For example, the inside diameter of the proximal end of the first hollow member 22 can be greater than the inside diameter of the distal end. Alternatively, or additionally, the inside diameter of the distal end of the second hollow member 28 can be less than the inside diameter of the proximal end. Such variations can be advantageous in inhibiting over-advancement of a medical instrument. In other embodiments, the inside diameters of both the first and second elongated hollow members 22, 28 are large enough to allow for insertion of a medical device therethrough.

The first elongated hollow member 22 can have an inside diameter ranging from 24 Fr to 30 Fr (e.g., in even sizes: 24, 26, 28, and 30 Fr). In some embodiments, the second elongated hollow member 28 can have an outside diameter sized to fit within the inside diameter of the first elongated hollow member (e.g., an outside diameter ranging from 24 Fr to 30 Fr). The wall thickness of the elongated hollow members 22, 28 generally varies depending upon the rigidity of the material used to form the members 22, 28. The wall thickness should be as thin as possible to provide a maximum working channel through the bore of the sheath assembly 10, while requiring a minimal diameter access tract. For example, the wall thickness can be 0.025 inch, +/−0.002 inch.

Generally, the distal end 24 of the first elongated hollow member 22 is adapted to facilitate insertion into the body 12. In one embodiment, the distal end 24 includes a beveled, or chamfered edge 36. The bevel 36 tapers the transition from an outside diameter of the second elongated member 28 to the outside diameter of the first member 22, eliminating any abrupt transition (e.g., sharp corner) in the outside diameter. Other configurations (not shown) for treating the distal end 24 include removing any abrupt transitions and/or exposed corners, by providing a radius thereon. Thus, as the variable length sheath assembly 10 is advanced along a tract 14, the bevel 36 reduces any likelihood that the sheath assembly 10 may catch and/or tear, or otherwise damage the walls of the tract 14.

Similarly, the proximal end 32 of the second elongated hollow member 28 is adapted to facilitate insertion and removal of medical instruments 35. In one embodiment, the proximal end 32 includes a beveled, or chamfered edge 38. The bevel 38 tapers the transition from the inside diameter of the second member 28 to the first 22, eliminating any abrupt transition in inside diameter. Other configurations (not shown) for treating the proximal end 32 include removing any abrupt transitions and/or exposed corners, by providing a radius thereon. Thus, as a medical instrument 35 is advanced along the interior of the variable length sheath assembly 10, the bevel 38 reduces any likelihood that the instrument will snag the sheath assembly 10, thereby reducing the chance that the sheath assembly 10 will become unintentionally dislodged or otherwise disturbed once seated.

In some embodiments, the variable length sheath assembly 10 includes a fitting at its proximal end 26 located outside of the patient's body. The fitting can include a flair 40, or cone, to facilitate manipulation of medical instruments and/or fluids into the sheath assembly 10. The cone has distal and proximal ends and is tapered toward the distal end. The cone has an opening at its proximal end for providing access to its interior. The cone's distal end is coupled to the sheath's proximal end 26. The diameter of the aperture at the cone's proximal end is larger than the diameter at its distal end, thereby facilitating insertion of medical devices to the sheath assembly 10 by guiding the devices to the bore of the sheath 10.

Additionally, or alternatively the fitting can include a flange 42. The flange 42 provides a secure surface that can be grasped by the physician and used to manipulate the variable length sheath assembly 10 during a length adjustment procedure and during insertion and removal procedure from a patient's body 12. Additionally, the flange 42 can serve as an anchor upon which medical instruments can be fastened. For example, an arthroscope can be clamped to the flange 42 to secure it during a medical procedure. Once secured, the scope can provide stable imagery while other medical instruments, such as a stone retrieval device, are manipulated within the sheath assembly 10. Although a flair 40 and/or a flange 42 can facilitate manipulation of the sheath assembly 10 and provide a support for anchoring medical instruments, neither the flair 40 nor the flange 42 are required. The portion of the variable length sheath assembly 10 remaining exposed outside of the patient's body 12, without any additional fittings, or features can also serve as a handle to be grasped for positioning and manipulating the sheath assembly 10, and can serve as an anchor upon which medical instruments can be fastened.

Generally, the variable length sheath assembly 10 is formed from a material selected to provide sufficient rigidity to maintain the tract 14 open. In some embodiments the material is formed from a semi-rigid material, capable of maintaining the tract 14 open, while allowing some flexibility. Flexibility is advantageous during insertion and removal of the sheath assembly 10 and in allowing the sheath assembly 10 to adapt to bodily contours. Rigid materials include metals and high-density plastics. Semi-rigid materials include polytetrafluoroethylene (PTFE), fluorinated ethylene propylene (FEP), polyethylene, some plastics, and combinations thereof. Materials including PTFE and FEP provide the added benefit of being slippery. It is desirable for the variable length sheath assembly 10 to have a substantially smooth external surface to facilitate its insertion into and removal from the patient's body 12.

As already discussed, the length adjustment element 34 adjustably fastens together the first and second elongated hollow members 22 and 28. In some embodiments, the length adjustment element 34 includes the distal end 24 and the proximal end 28. In these embodiments, there is generally a variable overlap of the distal and proximal ends 24 and 28 represented by the measurement, $L_O$. In other embodiments, the length adjustment element 34 is separate from the first and second members 22 and 28.

Figure 3C:
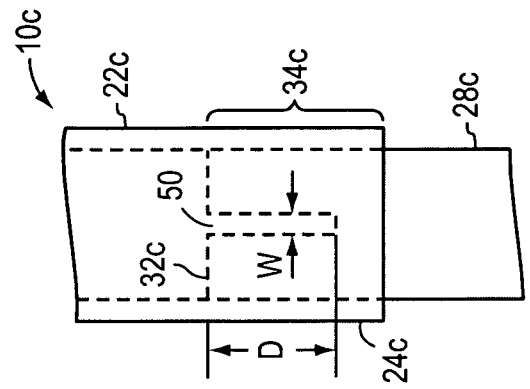
FIGS. 3A through 3G illustrate a cross-sectional views of alternative embodiments of the length-adjustment member illustrated in FIG. 1.
Figure 3B:
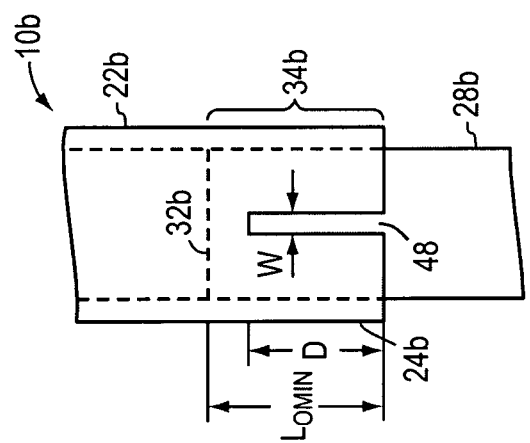
Figure 3A:
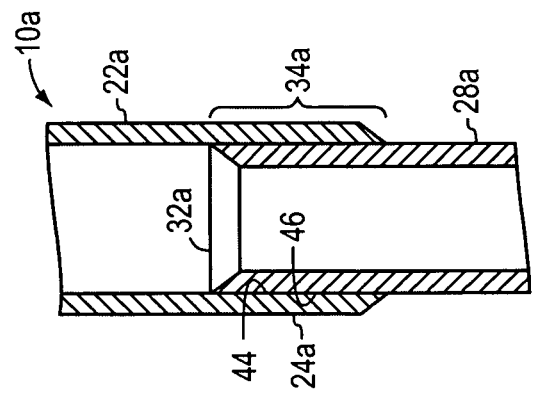

Referring now to FIGS. 3A through 3G, alternative embodiments of various length adjustment elements 34 are illustrated. Referring to FIG. 3A, in one embodiment of a variable length sheath assembly 10*a*, a distal end 24*a* of a first hollow member 22*a* coaxially overlaps a proximal end 32*a* of a second elongated hollow member 28*a*. Any internal surface 44 of the distal end 24*a* is in frictional communication with an external surface 46 of the proximal end 32*a*. Dimensions of the relative diameters as well as the selection of materials (e.g., plastic) and external finishes (e.g., smooth), and the amount of overlap, $L_O$, control an associated coefficient of friction between the mating surfaces 44 and 46. Generally, the coefficient of friction is selected to be low enough to allow for relative movement of the two elongated hollow members 22 and 28, thereby allowing a variation of the overall length of the variable length sheath assembly 10, yet high enough to securely fasten the two members 22 and 28 together under normal operating conditions.

In some embodiments, at least one of the distal and proximal ends 24 and 28 define a slot. For example, referring to FIG. 3B, in one embodiment, a distal end 24*b* includes one or more slots 48 extending axially along a first elongated hollow member 22*b* from the tip of the distal end 24*b* for a predetermined length. The length and width of the one or more slots 48 alter a coefficient of friction between the first and second elongated hollow members 22*b* and 28*b*. In some embodiments, the length, D, of the slot 48 is selected to be less than a minimum anticipated operational overlap $L_{omin}$. Such a restriction on the dimension D is useful for fluid-tight embodiments by reducing the possibility of a leak occurring from the slot 48, and reducing the occurrence of potential snags for medical instruments. In another embodiment, referring now to FIG. 3C, a slot 50 can be fashioned on a proximal end 32*c* of a second elongated hollow member 28*c*. Functionally, the internal slot 50 behaves as the external slot 48, providing similar length adjustment capabilities. In other embodiments, one or more external slots 48 can be combined with one or more internal slots 50.

Figure 3D:
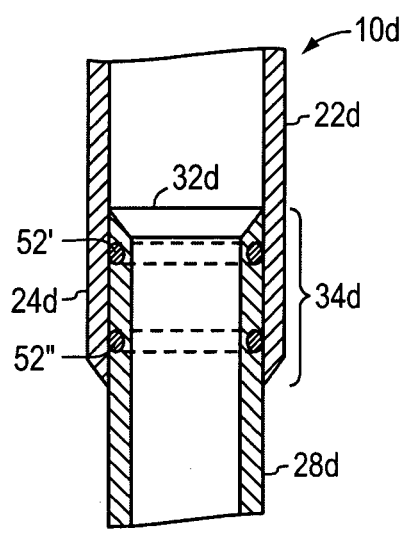

Referring to FIG. 3D, one embodiment of a length adjustment element 34*d* includes one or more elastomeric elements 52', 52" (generally 52) disposed between an overlapping distal end 24*d* and proximal end 32*d*. The elastomeric elements 52 are in frictional communication with both an interior surface of the distal end 24*d* and an exterior surface of the proximal end 32*d*, thereby fastening together a first and second elongated hollow members 22*d* and 28*d*.

In one embodiment, the elastomeric elements 52 include particles, such as spheroids or cylinders, secured within detents provided in either of the distal and proximal ends 24*d* and 32*d*. The detents fixedly attach the elastomeric elements 52 to the end 24*d*, 32*d* having the detents, while allowing a portion of the elastomeric elements 52 to remain exposed. The exposed portion of the elastomeric elements 52 is in frictional communication with the other of the respective ends 24*d*, 32*d*. In some embodiments, the elastomeric elements 52 are washers, such as "O-rings" extending circumferentially around the intersection of the ends 24*d* and 32*d*. O-rings are capable of providing the additional feature of being fluid-tight. The number and diameter of the O-rings controls a coefficient of friction between the two ends 24*d* and 32*d*. Adding more O-rings, and/or using O-rings with a thicker diameter increases the resulting coefficient of friction.

Figure 3E:
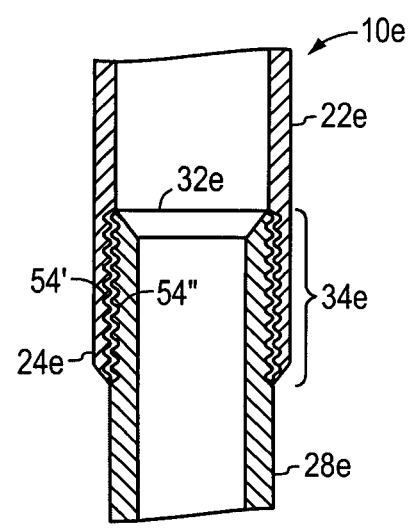

In another embodiment of a variable length sheath assembly 10*e*, referring to FIG. 3E, at least a portion of each of a distal end of a first elongated hollow member 22*e* and a proximal end 32*d* of a second elongated hollow member 28*e* are configured with mating threads 54' 54" (generally 54). The threads extend about the circumference of each respective end 24*e*, 32*e*, thereby allowing for the elongated hollow members 22*e* and 28*e* to be adjustably joined together. Rotation of the two elongated hollow members 22*e* and 28*e* in an opposite sense with respect to each other results in an adjustment of the overall length of the variable length sheath assembly 10*e*. Thus, tightening the threads shortens the length, whereas loosening the threads extends it. The number and pitch of the threads can be varied to provide a coarser or finer resolution in length variability. Additionally, a relatively fine thread, with a minimum overlap of more than the first several threads also provide to some degree a fluid-tight seal. The threads can be pretreated with a sealant, such as a silicon, to further enhance a fluid-tight seal.

Figure 3F:
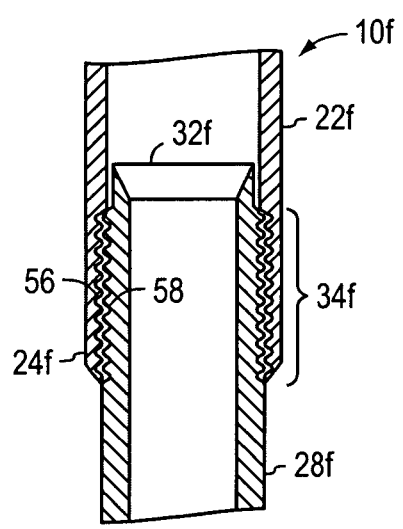
Figure 3G:
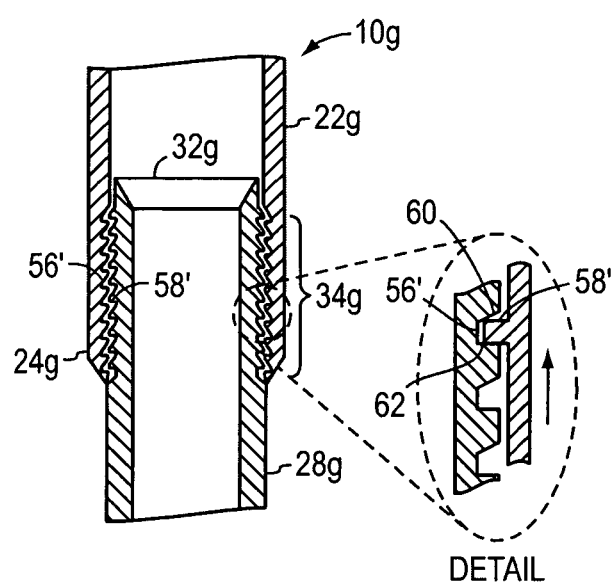

Referring to FIGS. 3F and 3G, alternative embodiments of variable length sheath assemblies 10*f* and 10*g* are illustrated having notch and detent systems. FIG. 3F illustrates a bi-directional notch and detent system in which a series of notches 56 are formed along at least a portion of the overlap between a distal end 24*f* of a first elongated hollow member 22*f* and a proximal end 32*f* of a second elongated hollow member 28*f*. The notches 56 can extend about the entire circumference of the respective end 24*f*, 32*f*, or over a portion thereof. The bi-directional notches 56 are substantially symmetrical in cross section (e.g., triangular), thereby allowing for the translation of a detent 58 in either direction across the profile of the notch 56. The detent 56 can also extend about the entire circumference of the respective end 24*f*, 32*f*, or over a portion thereof, as long as the detent 56 is in communication with the notches 56. The length of the sheath assembly 10*f* remains fixed when the detent 56 is seated within the vertex of the notch 58. As the two elongated hollow members 22*f* and 28*f* are translated in opposite directions with respect to each other, the detent 58 is translated over the apex between the notch 56 and its adjacent notch 56' and into the vertex of the adjacent notch 56', again fixing the adjusted length. The adjustment process can be repeated again in either direction to expand and/or contract the overall length of the sheath assembly 10*f*. The amount of adjustability is determined by the extent of the notches along the respective end 24*f*, 32*f*. That is, if the notches extend for 5 cm along the end 24*f*, 32*f*, then the overall length of the sheath assembly 10*f* can be adjusted to within 5 cm. In some embodiments, multiple detents 58 are provided, each detent 58 engaging a different notch 56 of the several notches.

FIG. 3G illustrates a unidirectional notch and detent system in which asymmetric notches 56' are provided in place of the bi-directional notches 56 of FIG. 3F. In one embodiment, illustrated in the detail of FIG. 3G, the asymmetric notches 56' have a positive slope along a first side 60 of the notch 56' and an infinite or negative slope along a second side 62 of the notch 56'. A detent 58' can rest within the vertex of the notch 56' providing a fixed length. In operation, the detent 58' can be translated along the first side 60, progressing along the positive slope until the detent 58' comes to rest in an adjacent notch 56", thereby allowing for a length adjustment in a first direction. A force attempting to translate the detent 58' in an opposite direction along the second side 62 is met with resistance prohibiting such movement.

In some embodiments it is desirable for the length of the variable length sheath assembly 10 to remain fixed, once adjusted. For example, once inserted into a patients body 12, the sheath assembly 10 can be subjected to compressive and/or tensile forces that would otherwise adjust the length of the sheath assembly 10. The unidirectional variable length sheath assembly 10*g* of FIG. 3G naturally resists compressive forces once adjusted. For example, in one embodiment, the sheath assembly is initially delivered having a minimum length. As described above, the unidirectional notch-and-detent system allows for the sheath assembly length to be extended, as required, prior to insertion into a patient's body 12. Once inserted, the unidirectional nature of the notch-and-detent system prohibits retraction of the sheath assembly 10 and maintains a fixed length, even as force is exerted on an exposed proximal end of the sheath assembly 10.

Figure 4A:
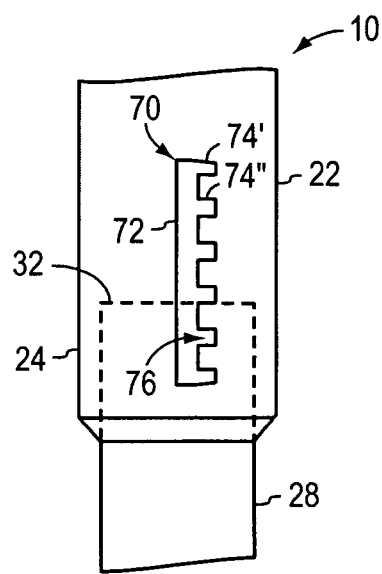
FIGS. 4A and 4B illustrate cross-sectional views of alternative embodiments of a length-adjustment locking mechanism.

FIG. 4A illustrates an alternative embodiment for an adjustment element locking mechanism to secure the length of a sheath assembly 10 once selected. In this embodiment, one of the overlapping proximal and distal ends 32 and 24 is configured with a trough 70 formed within a wall of the respective elongated hollow member 28, 22, and having a predetermined shape. For example, a trough 70 is formed within the interior of the distal end 24 of the first elongated hollow member 22. The trough 70 includes an axial element 72 extending axially for a predetermined length along the inside surface. Connected to the axial element 72 are multiple radial elements 74', 74" (generally 74) extending for a predetermined angle along the internal circumference of the inside surface. Mating with the trough 70 is a post 76 fixedly attached to the exterior of the proximal end 32 of the second elongated hollow member 28. The two elongated hollow members 22, 28 are manipulable with respect to each other, but relative motion is limited to the path formed by the trough 70. As the post 76 is translated along the axial element 72, the length of the variable length sheath assembly 10 can be varied. When a selected length is obtained, the elongated hollow members 22, 28 are rotated with respect to each other, such that the post 76 travels into the nearest radial element 74. As force is then applied along the axis of the sheath assembly 10, the interference fit between the post 76 and the edges of the radial trough 74 maintains the preselected sheath assembly length.

Figure 4B:
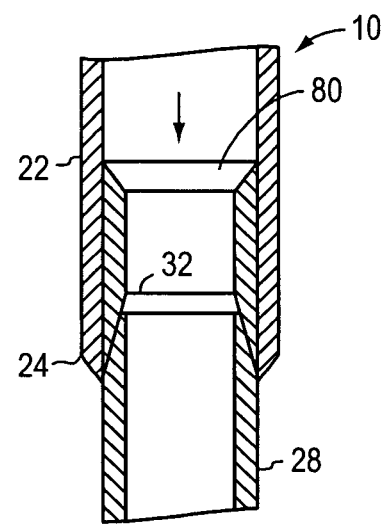

In another embodiment, referring to FIG. 4B, a wedge 80 is provided between the overlapping proximal 32 and distal 24 ends of the elongated hollow members 28 and 22. In operation, the length of the variable length sheath assembly 10 is first selected by sliding the overlapping portions of the elongated hollow members 22 and 28 with respect to each other. Once a desired length is achieved, the wedge 80 is driven between the overlapping portions of the two members 22 and 28, thereby providing an interference fit and securing the selected length. A wedge 80 inserted with adequate force secures the selected length under the normal compressive and tensile forces encountered during use. In one embodiment, the wedge 80 is an annular wedge. The annular wedge can also have a bevel or chamfer along its exposed end to facilitate insertion and removal of the sheath assembly 10 and/or medical instruments. In one embodiment, as illustrated in FIG. 4B, the wedge 80 is inserted from the interior of the sheath assembly. In another embodiment, the wedge 80 is inserted from the exterior of the sheath assembly (not shown).

Figure 5A:
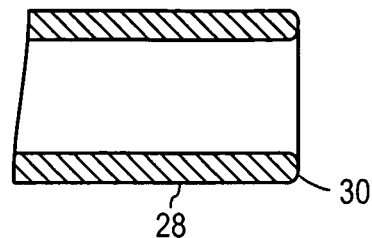
FIGS. 5A through 5C illustrate cross sectional views of alternative embodiments of the distal end of the adjustable sheath assembly illustrated in FIG. 1.
Figure 5B:
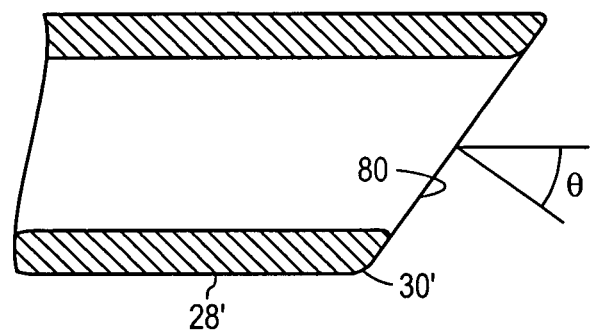
Figure 5C:
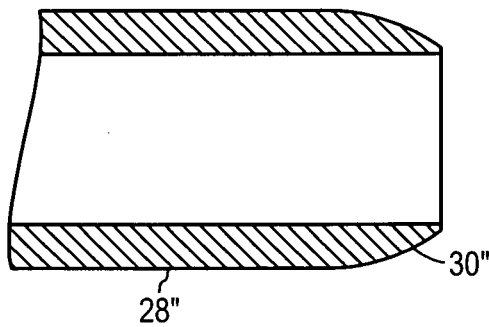

The distal end 30 of the second elongated member 28 of the variable length sheath assembly 10 can be adapted to facilitate insertion into, removal from, and general manipulation within the patient's body 12. For example, referring to FIG. 5A, the tip of the distal end 30 can be beveled or chamfered, thereby removing any sharp edges. Referring to FIG. 5B, the plane containing the face 80 of the opening of the distal end 30 can be formed such that a normal drawn outward from the plane 80 forms an acute angle $\theta$ with the axis of the member 28. Additionally, referring to FIG. 5C, the exterior portion of the distal end 30 can be tapered towards the tip.

Figure 6:
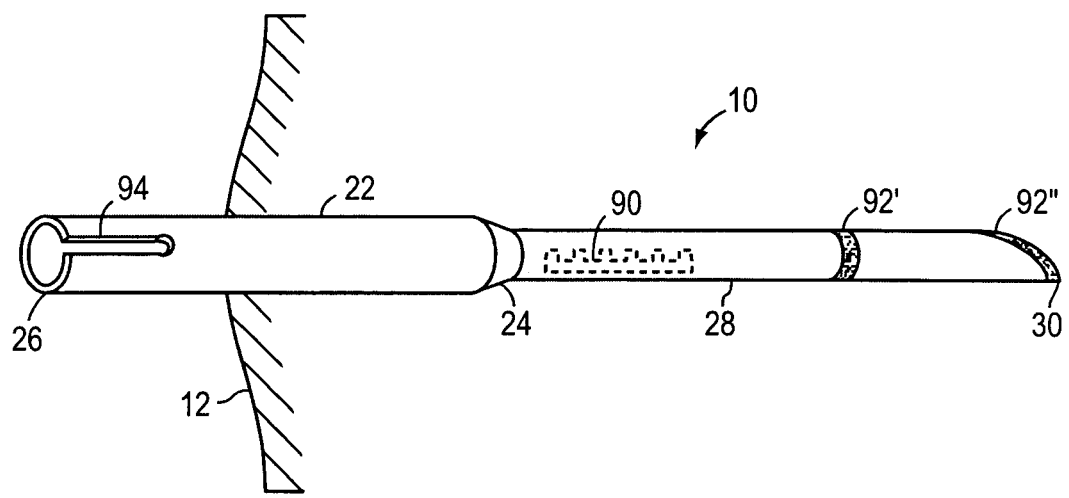
FIG. 6 illustrates a perspective view of an adjustable sheath assembly having additional features.

Additional features useful for sheath applications can be combined with the above-described embodiments of a variable length sheath assembly 10. For example, referring to FIG. 6, in one embodiment, a variable length sheath assembly 10 includes a human-readable scale 90 upon at lest one of a first and a second elongated hollow members 22 and 28. The scale can be used by a physician to facilitate selecting a length for the variable length sheath assembly 10 prior to insertion into a patient's body 12. The scale can be painted, inked, and/or etched into the respective member 22, 28.

In some embodiments, the sheath assembly 10 can be formed from a radio transparent material such as plastic. In other embodiments, the sheath assembly 10 can be formed from a radiopaque material such as metal-coated plastic. In still other embodiments, the sheath assembly 10 can be formed from a radio transparent material and contain one or more radiopaque markings 92', 92". Such an embodiment allows for precise positioning of the sheath assembly 10 using a radiograph, while also allowing for observation of medical instruments being used within the sheath assembly.

Additionally, the proximal end 26 of the first elongated hollow member 22 can include features adapted for securing medical instruments. For example, the proximal end 26 can include a fastener, such as a retaining slot 94 providing an interference fit for securing a medical instrument, such as a guide wire.

The elements of the variable length sheath assembly 10 can be manufactured using standard injection molding techniques. Alternatively, the elements of the variable length sheath assembly 10 can be formed using extrusion techniques combined with machining of the various details, such as the threads, bevels, notches, etc.

Thus, a variable length sheath assembly 10 can be fitted to patients of various sizes, including small children, and/or obese patients, allowing a physician to access the external end of the sheath assembly, while the sheath remains securely situated at a treatment area within the patient's body. The adjustable sheath assembly is sized to accept medical devices, thereby allowing a physician to perform a diagnosis and/or medical procedure at the treatment site in a minimally invasive manner, and without the complications and risks associated with using a sheath that is improperly sized.

While the invention has been particularly shown and described with reference to specific preferred embodiments, it should be understood by those skilled in the art that various changes in form and detail may be made therein without departing from the spirit and scope of the invention as defined by the appended claims.

What is claimed is:

1. A medical device adapted for insertion into a body of a patient for maintaining a passageway therein, the device comprising:
    a first hollow member having a proximal end, a distal end, and defining a lumen therethrough and a longitudinal axis, at least a portion of the proximal end configured to remain outside of the body;
    a second hollow member having a proximal end and a distal end and being disposable within the lumen of the first hollow member for slidable movement along the longitudinal axis of the first hollow member, the second hollow member defining a lumen sized to receive a medical instrument therethrough; and
    a wedge disposable within the lumen of the first hollow member, the wedge slides between positions including a first position in which the wedge is disposed entirely within the lumen of the first hollow member and is spaced from the second hollow member and a second position in which the wedge is disposed entirely within the lumen of the first hollow member and contacts the first hollow member and second hollow member to wedge the members together to inhibit relative axial movement of the two members.

2. The medical device of claim 1, wherein at least one of the first hollow member and the second hollow member comprises a cylinder.

3. The medical device of claim 1, wherein at least one of the first hollow member and the second hollow member is comprised of a semi-rigid material.

4. The medical device of claim 1, wherein at least one of the first hollow member and the second hollow member is comprised of a material selected from the group including polytetrafluoroethylene (PTFE), fluorinated ethylene propylene (FEP), polyethylene, plastics, and combinations thereof.

5. The medical device of claim 1, wherein the first hollow member defines an inner diameter, the second hollow member defines an outer diameter, the inner diameter of the first hollow member being greater than the outer diameter of the second hollow member.

6. The medical device of claim 1, wherein the medical instrument is a catheter.

7. The medical device of claim 1, wherein the distal end of the first hollow member includes a beveled edge adapted to facilitate insertion into the body.

8. The medical device of claim 1, wherein the distal end of the second hollow member defines an end face, the end face being adapted to facilitate insertion into the body.

9. The medical device of claim 8, wherein the end face defined by the distal end of the second hollow member defines a plane non-orthogonal to a longitudinal axis defined by the second hollow member.

10. The medical device of claim 8, wherein the end face includes a chamfered edge adapted to facilitate manipulation within the body.

11. The medical device of claim 1, wherein an interior surface of the distal end of the first hollow member overlaps and is in frictional communication with a portion of an exterior surface of the proximal end of the second hollow member.

12. The medical device of claim 1, wherein the proximal end of the second hollow member defines a slot that extends axially along the second hollow member, thereby enabling a radial deformation of the proximal end of the second hollow member.

13. The medical device of claim 1, wherein an elastomeric member is disposed between the distal end of the first hollow member and the proximal end of the second hollow member, the elastomeric member being in frictional communication with both the distal end of the first hollow member and the proximal end of the second hollow member.

14. The medical device of claim 1, further comprising a radiopaque marking adapted to facilitate positioning of the medical device at a predetermined location within the body.

15. The medical device of claim 1, further comprising a marking upon at least one of the first hollow member and the second hollow member, the marking being adapted to facilitate adjustment of a combined length of the first hollow member and the second hollow member.

16. The medical device of claim 1, further comprising a fastener at the proximal end of the first hollow member adapted for securing a guide wire device.

17. The medical device of claim 16, further comprising a retaining slot providing an interference fit for securing the guide wire device.

18. The medical device of claim 1, wherein the first hollow member is in substantially fluid tight communication with the second hollow member.

19. The medical device of claim 1, further comprising a washer adapted for maintaining a substantially fluid-tight seal between the first hollow member and the second hollow member.

20. The medical device of claim 1, wherein a combined length of the first hollow member and the second hollow member is longer than a length of the first hollow member when the wedge is in its second position.

21. The medical device of claim 1, wherein the second hollow member has a first position with respect to the first hollow member and a second position with respect to the first hollow member, the second hollow member being configured to move between the first position and the second position when the wedge is in its first position.

22. The medical device of claim 1, wherein the distal end of second hollow member is disposed apart from the first hollow member when the wedge is in the second position.

23. The medical device of claim 1, wherein at least a portion of the second hollow member extends distally from the distal end of the first hollow member when the wedge is in its second position.

24. The medical device of claim 1, wherein the wedge is formed by an injection molding technique.

25. A medical device adapted for insertion into a body of a patient for maintaining a passageway therein, the device comprising:
    a first hollow member for providing at least a portion of an unobstructed passageway from outside of the patient's body to the inside of the patient's body when inserted therein, the first hollow member having a sidewall defining a groove, the groove having a longitudinal portion and at least three notches; and a second hollow member in adjustable communication with the first hollow member for extending the unobstructed passageway provided in part by the first hollow member to a predetermined internal location beyond a distal end of the first hollow member, the second hollow member having a post configured to be disposed within the groove of the first hollow member, the post being configured to be movable between the longitudinal portion of the groove and the at least three notches of the groove, the post being configured to be slidable along the longitudinal portion of the groove when the second hollow member is adjusted with respect to the first hollow member.

26. The medical device of claim 25, wherein one end of the first hollow member is in slidable communication with one end of the second hollow member for adjusting an overall length of the combined first hollow member and second hollow member.

27. The medical device of claim 25, wherein the first hollow member has a proximal end and a distal end, the proximal end comprising a flange for attaching medical instruments thereto.

28. The medical device of claim 25, wherein the second hollow member does not move with respect to the first hollow member along the longitudinal axis defined by the first hollow member when the post is disposed within one of the plurality of notches of the groove.

29. The medical device of claim 25, wherein at least one of the first hollow member and the second hollow member is sized to accept a medical instrument.

30. The medical device of claim 25, wherein each notch of the plurality of notches defines an axis non-parallel to the longitudinal axis defined by the first hollow member.

31. The medical device of claim 25, wherein the second hollow member is in a locked position with respect to the first hollow member when the post is disposed within one of the plurality of notches of the groove.

32. The medical device of claim 25, wherein a distal end of the second hollow member defines an end face, the end face defining a plane non-orthogonal to a longitudinal axis defined by the second hollow member.

33. The medical device of claim 25, further comprising a radiopaque marking adapted to facilitate positioning of the medical device at a predetermined location within the body.

34. The medical device of claim 25, further comprising a marking upon at least one of the first hollow member and the second hollow member, the marking being adapted to facilitate adjustment of a combined length of the first hollow member and the second hollow member.

35. The medical device of claim 25, further comprising a fastener at a proximal end portion of the first hollow member, the fastener adapted for securing a guide wire device.

36. The medical device of claim 35, further comprising a retaining slot providing an interference fit for securing the guide wire device.

* * * * *